United States Patent
Takeshima

(10) Patent No.: US 10,215,822 B2
(45) Date of Patent: Feb. 26, 2019

(54) IMAGE PROCESSING APPARATUS AND MAGNETIC-RESONANCE IMAGING APPARATUS

(71) Applicant: TOSHIBA MEDICAL SYSTEMS CORPORATION, Otawara-shi, Tochigi (JP)

(72) Inventor: Hidenori Takeshima, Kanagawa (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 563 days.

(21) Appl. No.: 14/843,053

(22) Filed: Sep. 2, 2015

(65) Prior Publication Data

US 2015/0369893 A1 Dec. 24, 2015

Related U.S. Application Data

(63) Continuation of application No. PCT/JP2014/070388, filed on Aug. 1, 2014.

(30) Foreign Application Priority Data

Aug. 8, 2013 (JP) .................... 2013-165470

(51) Int. Cl.
  *G01R 33/54* (2006.01)
  *A61B 5/055* (2006.01)
  (Continued)

(52) U.S. Cl.
  CPC .............. *G01R 33/54* (2013.01); *A61B 5/055* (2013.01); *G01R 33/4818* (2013.01);
  (Continued)

(58) Field of Classification Search
  CPC ................ G01R 33/54; G01R 33/4818; G01R 33/5611; G01R 33/56545; G01R 33/4824; G01R 33/56; A61B 5/055; A61B 2576/00
  (Continued)

(56) References Cited

U.S. PATENT DOCUMENTS 7,282,917 B1   10/2007   Brau et al.
7,688,068 B2   3/2010    Beatty
(Continued)

FOREIGN PATENT DOCUMENTS

JP   2008-200478   9/2008

OTHER PUBLICATIONS

Int'l. Search Report for PCT/JP2014/070388, dated Nov. 4, 2014, one page.
(Continued)

*Primary Examiner* — Melissa Koval
*Assistant Examiner* — Courtney McDonnough
(74) *Attorney, Agent, or Firm* — Nixon & Vanderhye P.C.

(57) ABSTRACT

A magnetic resonance imaging apparatus according to an embodiment includes a processor, and a memory that stores processor-executable instructions. When the instructions are executed by the processor, the instructions cause the processor to give a sample value to at least a part of sampling positions having no sample value in first k-space data so as to create a second k-space data, the first k-space data having a sample value at a part of sampling positions on a k-space. The instructions cause the processor to create a first image from the first k-space data and a second image from the second k-space data. The instructions cause the processor to derive weighting factors for the first image and the second image. The instructions cause the processor to calculate a
(Continued)

magnetic resonance image by performing weighted addition using the weighting factors on the first image and the second image.

10 Claims, 11 Drawing Sheets

(51) Int. Cl.
  *G01R 33/561* (2006.01)
  *G01R 33/565* (2006.01)
  *G01R 33/48* (2006.01)

(52) U.S. Cl.
  CPC .... *G01R 33/5611* (2013.01); *G01R 33/56545* (2013.01); *A61B 2576/00* (2013.01); *G01R 33/4824* (2013.01)

(58) Field of Classification Search
  USPC .......................................................... 324/309
  See application file for complete search history.

(56) References Cited

U.S. PATENT DOCUMENTS

| | | | |
|---|---|---|---|
| 8,026,720 | B1 | 9/2011 | Chen et al. |
| 8,170,315 | B2 | 5/2012 | Mistretta et al. |
| 2003/0001571 | A1* | 1/2003 | Wang ................ G01R 33/3415 324/309 |
| 2005/0264287 | A1* | 12/2005 | Griswold ........... G01R 33/5611 324/309 |
| 2010/0308824 | A1* | 12/2010 | Grady ................ G01R 33/5611 324/309 |
| 2011/0098552 | A1* | 4/2011 | Takai .................. G01R 33/561 600/410 |

OTHER PUBLICATIONS

Written Opinion for PCT/JP2014/070388, dated Nov. 4, 2014, three pages.

K. P. Pruessmann et al., "SENSE: Sensitivity Encoding for Fast MRI", MRM, vol. 42, pp. 952-962, 1999.

Mark A. Griswold et al., "Generalized Autocalibrating Partially Parallel Acquisitions (GRAPPA)", MRM, vol. 47, pp. 1202-1210, 2002.

A. C. S. Brau et al., "Comparison of Reconstruction Accuracy and Efficiency Among Autocalibrating Data-driven Parallel Imaging Methods", MRM, vol. 59, pp. 382-395, 2008.

A.C. Brau et al., "Simultaneous Calibration Scheme for Data-Driven Parallel Imaging Reconstruction", Proc. Intl. Soc. Mag. Reson. Med. 16, #1300, 1 pg. 2008.

N. Seiberlich et al., "Creation of Arbitrary Spatial Harmonics though the Combination of Orthogonal Weights (CASHCOW): A Generalized Direct GRAPPA Approach for Non-Cartesian Data", Proc. Intl. Soc. Mag. Reson. Med. 17, #2714, 1 pg., 2009.

* cited by examiner

IMAGE PROCESSING APPARATUS AND MAGNETIC-RESONANCE IMAGING APPARATUS

CROSS-REFERENCE TO RELATED APPLICATIONS

This application is a continuation of PCT international application Ser. No. PCT/JP2014/070388 filed on Aug. 1, 2014 which designates the United States, incorporated herein by reference, and which claims the benefit of priority from Japanese Patent Application No. 2013-165470, filed on Aug. 8, 2013, the entire contents of which are incorporated herein by reference.

FIELD

Embodiments described herein relate generally to an image processing apparatus and a magnetic resonance imaging apparatus.

BACKGROUND

A magnetic resonance imaging apparatus (hereinafter, "MRI apparatus" as appropriate) is an apparatus to visualize information inside a subject body into an image, using a nuclear magnetic resonance phenomenon. In the MRI apparatus, data called k-space data is acquired by sampling nuclear magnetic resonance signals from a specific atom (for example, hydrogen atom) present inside an object using coils. Moreover, the MRI apparatus reconstructs a magnetic resonance image (hereinafter, "MR image" as appropriate) by applying the Fourier transform on k-space data.

Nuclear magnetic resonance signals (hereinafter, "MR signals") are sampled as one-dimensional data. Therefore, to acquire two-dimensional, or three-dimensional reconstruction image, the MR apparatus repeats sampling of one-dimensional data on a k-space, and acquires k-space data necessary for reconstruction. If k-space data is sampled at the same resolution as the MR image (full sampling), reconstruction is enabled by applying the Fourier transform on the acquired k-space data. However, if full sampling is performed in the MRI apparatus, the imaging time is to be considerably long. Accordingly, techniques have been developed conventionally on in both an imaging technique and a reconstruction technique to achieve reduction of the imaging time.

For example, as a reconstruction technique to reduce the imaging time, there is a technique called parallel imaging (hereinafter, "PI" as appropriate) in which multiple coils are used and imaging of a subject body is performed with less samples than full sampling, and an MR image is reconstructed using difference in coil sensitivity of respective coils. As techniques of PI, sensitivity encoding (SENSE) and generalized auto calibrating partially parallel acquisition (GRAPPA) are widely known.

DETAILED DESCRIPTION

A magnetic resonance imaging apparatus according to an embodiment includes a k-space-data creating unit, an image creating unit, a deriving unit, and a calculating unit. The k-space-data creating unit gives a sample value to at least a part of sampling positions having no sample value in first k-space data so as to create a second k-space data, the first k-space data having a sample value at a part of sampling positions on a k-space. The image creating unit creates a first image from the first k-space data, and creates a second image from the second k-space data. The deriving unit derives weighting factors for the first image and the second image. The calculating unit calculates a magnetic resonance image by performing weighted addition using the weighting factors on the first image and the second image.

An MRI apparatus and an image processing apparatus according to each embodiment performs imaging with less samples than full sampling, and reconstructs an MR image using difference in coil sensitivity of respective coils, similarly to SENSE or GRAPPA. While most of the existing PI techniques are improved techniques of SENSE or GRAPPA, in the following a PI technique is provided by formulation that is different from the existing frameworks. The MRI apparatus and the image processing apparatus according to each embodiment are explained below with reference to the drawings. Embodiments are not limited to the embodiments below. Moreover, what is explained in each embodiment is similarly applicable to other embodiments in principle.

First Embodiment

Figure 1:
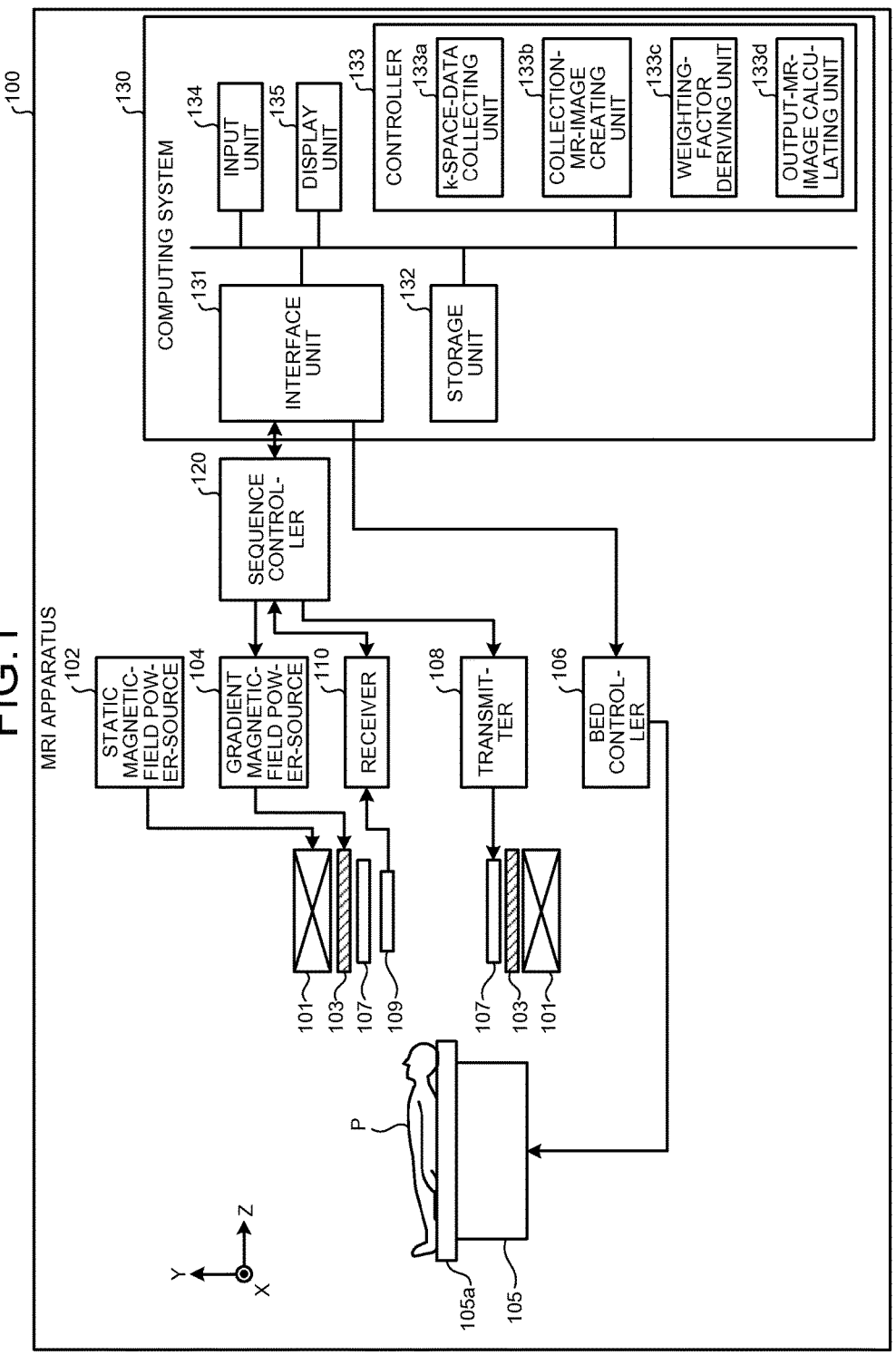
FIG. 1 is a functional block diagram of an MRI apparatus 100 according to a first embodiment.

FIG. 1 is a functional block diagram of an MRI apparatus 100 according to a first embodiment. As shown in FIG. 1, the MRI apparatus 100 includes a static magnetic-field magnet 101, a static magnetic-field power-source 102, a gradient magnetic-field coil 103, a gradient magnetic-field power-source 104, a bed 105, a bed controller 106, a transmission coil 107, a transmitter 108, a reception coil array 109, a receiver 110, a sequence controller 120, and a computing system 130. A subject P (for example, human body) is not included in the MRI apparatus 100.

The static magnetic-field magnet 101 is a magnet that is formed in a cylindrical shape with a hollow, and generates a static magnetic field in a space inside. The static magnetic-field magnet 101 is, for example, a super conducting magnet, or the like, and is supplied with an electric current from the static magnetic-field power-source 102 to be magnetized. The static magnetic-field power-source 102 supplies an electric current to the static magnetic-field magnet 101. The static magnetic-field magnet 101 may be a permanent magnet, and in this case, the MRI apparatus 100 is not required to be equipped with the static magnetic-field power-source 102. Furthermore, the static magnetic-field power-source 102 may be prepared separately from the MRI apparatus 100.

The gradient magnetic-field coil 103 is a coil that is formed in a cylindrical shape with a hollow, and is arranged inside the static magnetic-field magnet 101. The gradient magnetic-field coil 103 is formed with a combination of three coils corresponding to respective axes of X, Y, and Z that intersect at right angles with each other. These three coils receive an electric current individually from the gradient magnetic-field power-source 104 to generate a gradient magnetic field the magnetic field intensity of which varies along each of the axes, X, Y, and Z. Note that the direction of the Z axis is identical to a static magnetic field.

The gradient magnetic-field power-source 104 supplies an electric current to the gradient magnetic-field coil 103. The static magnetic fields of each of the axes, X, Y, and Z that are generated by the gradient magnetic-field coil 103 correspond, for example, to a slice-selecting gradient magnetic field Gs, a phase-encoding gradient magnetic field Ge, and a read-out gradient magnetic field Gr, respectively. The slice-selecting gradient magnetic field Gs is used to determine an imaging section arbitrarily. The phase-encoding gradient magnetic field Ge is used to vary the phase of an MR signal according to a spatial position. The read-out gradient magnetic field Gr is used to vary the frequency of the MR signal according to the spatial position.

The bed 105 includes a top panel 105a on which the subject P is mounted, and inserts the top panel 105a in a state that the subject P is mounted thereon into the hollow (imaging opening) of the gradient magnetic-field coil 103 under control by the bed controller 106. Usually, the bed 105 is arranged such that the longitudinal direction thereof is in parallel with the central axis of the static magnetic-field magnet 101. The bed controller 106 drives the bed 105 under control by the computing system 130 to move the top panel 105a in the longitudinal direction and the vertical direction.

The transmission coil 107 is arranged inside the gradient magnetic-field coil 103, and receives a radio frequency (RF) pulse from the transmitter 108 to generate a high-frequency magnetic field. The transmitter 108 supplies the RF pulse corresponding to a Larmor frequency that is determined based on a type of a subject atom and the intensity of a magnetic field, to the transmission coil 107.

The reception coil array 109 is arranged inside the gradient magnetic-field coil 103, and receives the MR signal that is emitted from the subject P by the influence of the high-frequency magnetic field. Upon receiving the MR signal, the reception coil array 109 outputs the received MR signal to the receiver 110. In the first embodiment, the reception coil array 109 is a coil array that has more than one reception coil.

The receiver 110 generates MR data based on the MR signal output from the reception coil array 109. Specifically, the receiver 110 generates the MR data by performing digital conversion on the MR signal that is output from the reception coil array 109. Furthermore, the receiver 110 transmits the generated MR data to the sequence controller 120. The receiver 110 can be equipped on a stand unit side having the static magnetic-field magnet 101, the gradient magnetic-field coil 103, and the like.

In the first embodiment, the MR signals output from respective coil elements (respective reception coils) of the reception coil array 109 are distributed and combined as necessary, to be output to the receiver 110 in a unit called channel or the like. Accordingly, the MR data is handled in channel in the process in a stage subsequent to the receiver 110. As for the relation between the total number of the coil elements and the total number of the channels, it can be identical, or the total number of the channels can be fewer than the total number of the coil elements, or oppositely, the total number of the channels can be more than the total number of the coil elements. Hereafter, when it is described as "channel", the process can be performed in each coil element, or can be performed in each channel in which coil elements are distributed and combined. The timing for distribution and combination is not limited to the timing described above. The MR signal or the MR data can be distributed and combined into a channel unit any time prior to the reconstruction processing of an image described later.

The sequence controller 120 performs imaging of the subject P by driving the gradient magnetic-field power-source 104, the transmitter 108, and the receiver 110 based on sequence information transmitted from the computing system 130. The sequence information defines a procedure for performing imaging. In the sequence information, the strength of electric power to be supplied to the gradient magnetic-field coil 103 by the gradient magnetic-field power-source 104 and timing for supplying electric power, the intensity of the RF pulse that is transmitted to the transmission coil 107 by the transmitter 108 and timing for applying the RF pulse, timing for detecting the MR signal by the receiver 110, and the like are defined.

Upon receiving the MR data from the receiver 110 as a result of imaging the subject P by driving the gradient magnetic-field power-source 104, the transmitter 108, and the receiver 110, the sequence controller 120 transfers the received MR data to the computing system 130.

The computing system 130 performs overall control of the MRI apparatus 100, data collection, image reconstruction, and the like, and includes an interface unit 131, a storage unit 132, a controller 133, an input unit 134, and a display unit 135.

The interface unit 131 transmits the sequence information to the sequence controller 120, and receives the MR data from the sequence controller 120. Moreover, the interface unit 131 stores the received MR data in the storage unit 132 when the MR data is received. The MR data stored in the storage unit 132 is arranged in the k-space by a k-space-data collecting unit 133a described later. As a result, the storage unit 132 stores k-space data of multiple channels.

The storage unit 132 stores the MR data that is received by the interface unit 131, k-space data that is arranged in the k-space by the k-space-data collecting unit 133a, image data that is generated by the controller 133, and the like. For example, the storage unit 132 is a random access memory (RAM), a semiconductor memory device such as a flash memory, a hard disk, an optical disc, or the like.

The input unit 134 accepts various kinds of instructions or information input by an operator. The input unit 134 is, for example, a pointing device such as a mouse and a trackball, a selecting device such as a mode switching switch, or an input device such as a keyboard. The display unit 135 displays various kinds of information such as spectrum data and image data under control by the controller 133. The display unit 135 is, for example, a display device such as a liquid crystal display.

The controller 133 performs overall control of the MRI apparatus 100. Specifically, the controller 133 generates the sequence information based on an imaging condition input by an operator through the input unit 134, and transmits the generated sequence information to the sequence controller 120, to control imaging. Furthermore, the controller 133 controls image reconstruction based on the MR data that is transmitted from the sequence controller 120 as a result of imaging, or controls display by the display unit 135. For example, the controller 133 generates the spectrum data and the image data by performing reconstruction processing such as the Fourier transform on the k-space data stored in the storage unit 132. For example, the controller 133 is an integrated circuit such as an application specific integrated circuit (ASIC) and a field programmable gate array (FPGA), or an electronic circuit such as a central processing unit (CPU) and a micro processing unit (MPU). The controller 133 includes, for example, a processor and a memory. The memory stores processor-executable instructions that, when executed by the processor, cause the processor to perform processes described later as being performed by the controller 133.

SENSE and GRAPPA that are one of the PI techniques are explained. In SENSE, a sensitivity map that indicates the sensitivity of each coil is collected in advance. Moreover, the k-space data is collected by undersampling relative to full sampling. When reconstruction is performed by applying the Fourier transform on undersampled k-space data, a fold-over image is acquired for each coil. In SENSE, a value obtained by dividing the sampling amount in full sampling by the sampling amount in undersampling is called "reduction factor", and is expressed as "R".

The reconstructed fold-over image is an image obtained by superimposing R pieces of fold-over signals. When the coil is expressed as "c=1, . . . , C", and a pixel value of a fold-over image of each coil is expressed as "ρ(c)", a pixel value of one pixel of interest in a fold-over image is expressed by following Equation (1). Moreover, a linear system in which Equation (1) of the number same as the number of the coils is aligned is expressed by Equation (2) using a matrix expression. An "output MR image" is an MR image of an object to be output.

$$\rho(c) = \sum_{p=1}^{R} s(c, p) \hat{f}(p) \quad (1)$$

p=1, R: position of a pixel corresponding to output MR image
s(c, p): sensitivity of each coil to output MR image
$\hat{f}(p)$: pixel value corresponding to ρ(c) in output MR image $$\rho = S\hat{f} \quad (2)$$

At this time, a solution obtained by the method of least squares weighted by a noise covariance matrix ψ of a coil is expressed by Equation (3). In SENSE, an output MR image is reconstructed by applying Equation (3) to each pixel.

$$\hat{f} = (S^*\psi^{-1}S)^{-1}S^*\psi^{-1}\rho \quad (3)$$

On the other hand, in GRAPPA, it is considered, for k-space data collected by multiple coils, that an unknown sample value is equal to weighted linear sum of sample values therearound. Moreover, in GRAPPA, for a region apart from the center of the k-space (peripheral region), regularly undersampling relative to full sampling is performed similarly to SENSE, and for a region close to the center of the k-space (center region), full sampling is performed unlike SENSE.

In GRAPPA, there are two steps: "calculation of weighting factors" and "creation of unknown sample values". At the step of "calculation of weighting factors", a weighting factor is estimated using a region in which full sampling has been performed. Specifically, in GRAPPA, when a sampling position on a k-space having sample values is expressed as "k", and a shift amount from "k" from a sampling position having a sample value is expressed as "b", it is considered that Equation (4) is true. Although a case in which k-space is of two dimensions is explained here, the same is applicable to a case of three dimensions.

$$F(k, c_{out}) = \sum_c \sum_b w(b, c, c_{out}) F(k+b, c) \quad (4)$$

"F(k, $c_{out}$)" is a sample value at the sampling position k in a coil $c_{out}$. Furthermore, "w(b, c, $c_{out}$)" is a weighting factor at the coil $c_{out}$ corresponding to the shift amount b and the coil c. Moreover, "F(k+b, c)" is a sample value sampled at a sampling position that is shifted by "b" from the sampling position "k" in the coil c.

Figure 2:
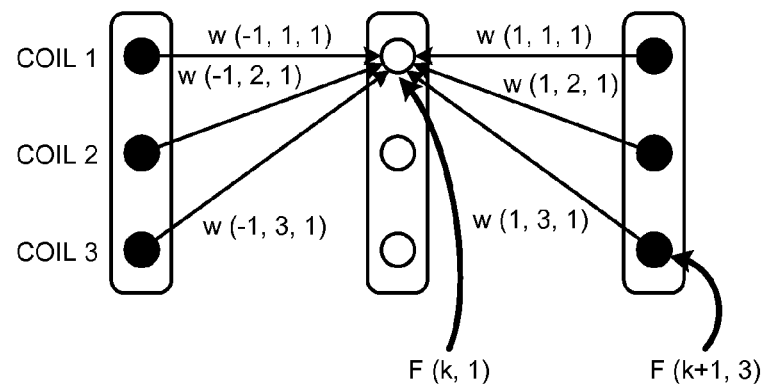
FIG. 2 is a diagram for explaining relation among sample values in GRAPPA.

FIG. 2 is a diagram for explaining relation among sample values in GRAPPA. FIG. 2 is to explain Equation (4) with examples of specific numeric values, and is only an example. As shown in FIG. 2, a sample value F(k, 1) is a sample value at the sampling position k in coil 1. Moreover, the sample value F(k+1, 3) is a sample value at a sampling position shifted by "1" from the sampling position "k" in coil 3. As shown in FIG. 2, the sample value F(k, 1) is expressed by a weighted liner linear sum of a sample value at a sampling position that is shifted by "1" from the sampling position "k" in each of coils 1 to 3, and a sample value at a sampling position that is shifted by "−1" from the sampling position "k" in each of coils 1 to 3. The weighting factors are w(1, 1, 1), w(1, 2, 1), w(1, 3, 1), w(−1, 1, 1), w(−1, 2, 1), and w(−1, 3, 1), respectively.

Because all sample values (namely, F(k, $c_{out}$) and F(k+b, c)) are known in the region in which full sampling has been performed, the weighted factor w(b, c, $c_{out}$) can be estimated by, for example, the method of least squares. At the step of creation of unknown sample values, the weighting factor acquired at the step of calculation of weighting factors is substituted into Equation (4), to generate an unknown sample value.

In the first embodiment, it is considered that an output MR image is expressed by weighted addition of multiple MR images having the same resolution as this output MR image. Moreover, in the first embodiment, a technique of giving data constraint equivalent to Equation (4) is explained as one example of condition to give constraint to a weighting factor in estimation of a weighting factor. Constraint equivalent to Equation (4) is a total sum of values (errors) obtained by squaring differences between the left side and the right side of Equation (4) with respect to all of the sampling positions k in a region in which full sampling is performed. However, even if the data constraint equivalent to Equation (4) is used in estimation of the weighting factor, the reconstruction processing of an output MR image is performed not by interpolation of sample values in a k-space, but by the weighted linear sum among MR images in the first embodiment, and accordingly, it is totally different from GRAPPA.

An output MR image has pixel values on grid points that are arranged for predetermined output resolution. However, the MRI apparatus 100 does not necessarily perform sampling on all of grid points corresponding to the output resolution when sampling of k-space data is performed. In the following, to perform sampling for all of grid points corresponding to output resolution is referred to as "full sampling" for convenience sake. Furthermore, a technique of performing sampling on all or some of grid points corresponding to output resolution is referred to as Cartesian sampling, and a technique of performing sampling on points including ones that are not grid points is referred to as non-Cartesian sampling.

Regardless of Cartesian sampling or non-Cartesian sampling, when sampling intervals are large, that is, when sample values are fewer than a sampling density that is required for reconstruction of an MR image, the reconstructed MR image has a pixel value in which multiple signals are superimposed by aliasing. In the PI technique, by using a coil sensitivity, a signal value on which aliasing is not performed is restored from superimposed signals.

In the first embodiment, considering a linear weight, an output MR image that is not subjected to aliasing (an object of restoration) is considered to be expressed in a form in which the MR image subjected to aliasing is weighted. Estimating the weighting factor, an output MR image is restored using the weighting factor.

Figure 3:
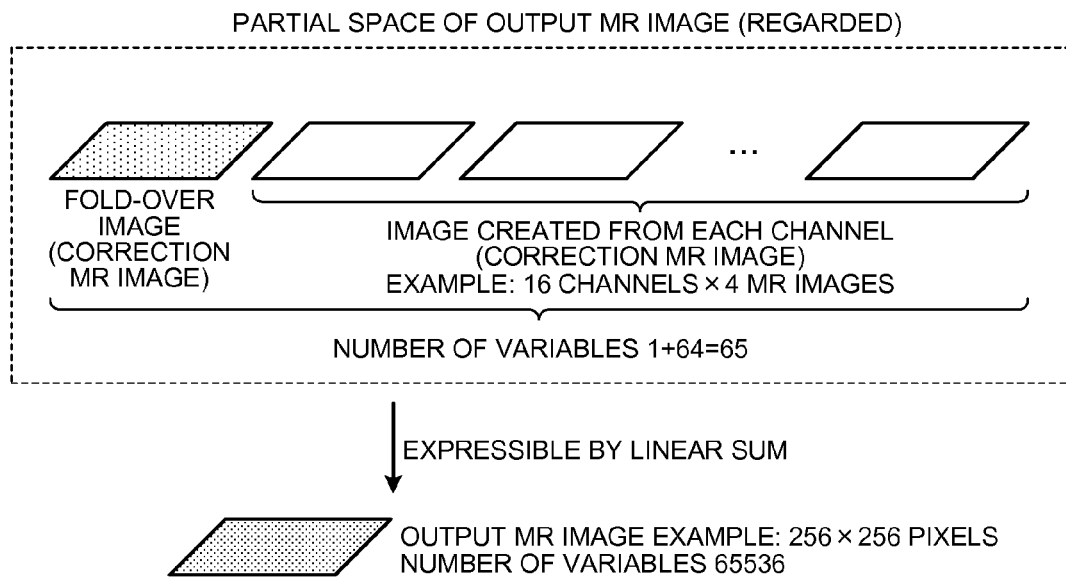
FIG. 3 is an explanatory diagram for a weighted linear sum of an MR image of the first embodiment.

FIG. 3 is an explanatory diagram for a weighted linear sum of an MR image in the first embodiment. Based on the concept of the PI, if an MR image is created based on data collected by multiple coils (channels), and an appropriate weighting factor is multiplied on the created MR image to perform composition, a reconstructed image without aliasing is supposed to be obtained. In other words, as shown in FIG. 3, it can be considered that an output MR image is present on a partial space in a space of output resolution that can be expressed by the weighted linear sum of multiple MR images that are created from data collected by multiple coils (channels). Furthermore, as one example of a method of estimating a weighting factor of a linear sum, estimation of a weighting factor using a constraint that is linked to coil sensitivity can be used. The purpose thereof is to acquire a desired reconstruction image, and a method of estimating a weighting factor of a linear sum is not necessarily required to be linked closely to coil sensitivity. Moreover, as shown in FIG. 3, when the resolution of an output MR image is 256×256 pixels, the number of variables thereof is 65536. On the other hand, suppose the number of channels is 16 and the number of correction MR images is 4, the number of variables thereof is 65 (including ones of fold-over images). When the technique in which an output MR image is expressed as a weighted linear sum of multiple MR images and the weight thereof is estimated is used, the number of variables to be estimated can be less compared to the technique in which all pixels are estimated.

More specifically, the MRI apparatus 100 according to the first embodiment collects k-space data with less samples than full sampling, and then performs some kind of processing on this k-space data to acquire another k-space data. The MRI apparatus 100 then acquires an output MR image without fold-over by weighted addition of an MR image with "fold-over" that is obtained from an original k-space data, and an MR image without fold-over that is obtained from another k-space data.

In the following, an MR image to be an object of weighted addition is referred to as correction MR image, and an MR image that is obtained by weighted addition of correction MR images is referred to as output MR image; however, these are only to distinguish therebetween for convenience sake of explanation. For example, the correction MR image may be output. Furthermore, for example, an MR image in which an output MR image is subjected to post processing may be output finally to the display unit 135 or the like.

The controller 133 includes the k-space-data collecting unit 133a, a correction-MR-image creating unit 133b, a weighting-factor deriving unit 133c, and an output-MR-image calculating unit 133d.

The k-space-data collecting unit 133a collects k-space data according to an imaging condition that is input by an operator. Specifically, the k-space-data collecting unit 133a accepts an input of various kinds of imaging conditions on graphical user interface (GUI), creates sequence information according to the accepted imaging conditions, and transmits the created sequence information to the sequence controller 120. Moreover, the k-space-data collecting unit 133a arranges MR data that is received from the sequence controller 120 in a k-space.

Note that the k-space-data collecting unit 133a according to the first embodiment collects k-space with less samples than full sampling, not of full sampling. For example, the k-space-data collecting unit 133a performs sampling at resolution same as full sampling in a central region of a k-space, and performs undersampling in a peripheral region of the k-space. The k-space data that is obtained by undersampling has sample values at some of sampling positions out of sampling positions on the k-space corresponding to full sampling. In the following, original k-space data that is collected by the k-space-data collecting unit 133a is referred to as imaging k-space data as appropriate, and thereby distinguished from another k-space data that is obtained by performing some kind of processing on the original k-space data.

The correction-MR-image creating unit 133b creates an MR image for correction to calculate an output MR image. Specifically, the correction-MR-image creating unit 133b performs processing of giving a sample value to at least a part of sampling positions that have no sample values on imaging k-space data with less samples than full sampling, thereby creating another k-space data. Furthermore, the correction-MR-image creating unit 133b creates a correction MR image from imaging k-space data, and creates a correction MR image also from the other k-space data that is obtained from the imaging k-space data. Details of processing by the correction-MR-image creating unit 133b are described later.

The weighting-factor deriving unit 133c derives a weighting factor relating to a correction MR image that is created by the correction-MR-image creating unit 133b. Details of processing by the weighting-factor deriving unit 133c are described later.

The output-MR-image calculating unit 133d performs weighted addition using the derived weighting factor that is derived from the weighting-factor deriving unit 133c on the correction MR image that is created by the correction-MR-image creating unit 133b, to calculate an output MR image. Details of processing by the output-MR-image calculating unit 133d are described later.

Before explanation of specific processing, formulation of processing in the first embodiment is performed. In the following, an output MR image is expressed by a vertical vector X, and N (N≥2) pieces of correction MR images having the same size as X are expressed by Xi, and a weighting factor (scalar value) is expressed by wi. The correction MR image Xi is an image having the same number of pixels as the output MR image X. In the following embodiment, the output MR image X is given by Equation (5). When the correction MR image Xi is given, the flexibility of the output MR image X does not exceed the number N of unknown weighting factors. Xm and Xn may be independent of or dependent on arbitrary values of m, n (m≠n).

$$X = \sum_i w_i X_i \quad (5)$$

As described, the output MR image X is a point on a space on which the output MR image can be expressed as a linear sum of the correction MR images Xi, and the weight to the correction MR image Xi is expressed by wi. In other words, a desired reconstruction image is required to be expressed as a linear sum of the correction MR images Xi for the output MR image to be the desired reconstruction image.

Therefore, in the following embodiment, a problem to obtain the output MR image X is regarded as a problem that includes a step of giving the correction MR image Xi and a step of deriving the weighting factor wi. Specifically, the correction-MR-image creating unit 133b creates the correction MR image Xi, and the weighting-factor deriving unit 133c derives the weighting factor wi. The output-MR-image calculating unit 133d then calculates the output MR image X using the correction MR image Xi and the weighting factor wi based on Equation (5).

When more than one output channel is present, an output MR image Xk is given by Equation (6) for a channel k=1, . . . , C. In this case, the correction-MR-image creating unit 133b creates a correction MR image Xi,k, and the weighting-factor deriving unit 133c derives a weighting factor wi,k. The output-MR-image calculating unit 133d then calculates the output MR image Xk using the correction MR image Xi,k and the weighting factor wi,k based on Equation (6). When more than one output channel is present, the same processing is applied to each of the channels k=1, . . . , C. In the following, it is expressed omitting the channel k for convenience sake of explanation, the following embodiment is applicable even when more than one output channel is present.

$$X_k = \sum_i w_{i,k} X_{i,k} \quad (6)$$

Figure 4:
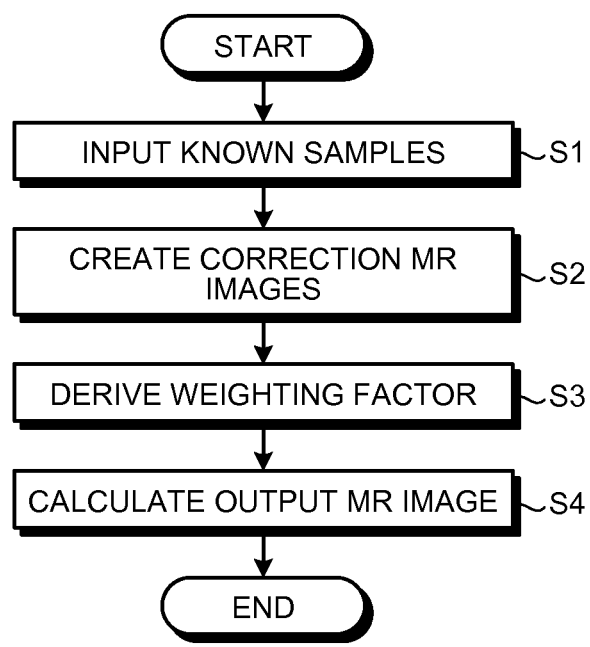
FIG. 4 is general flowchart of a processing procedure in the first embodiment.
Figure 5:
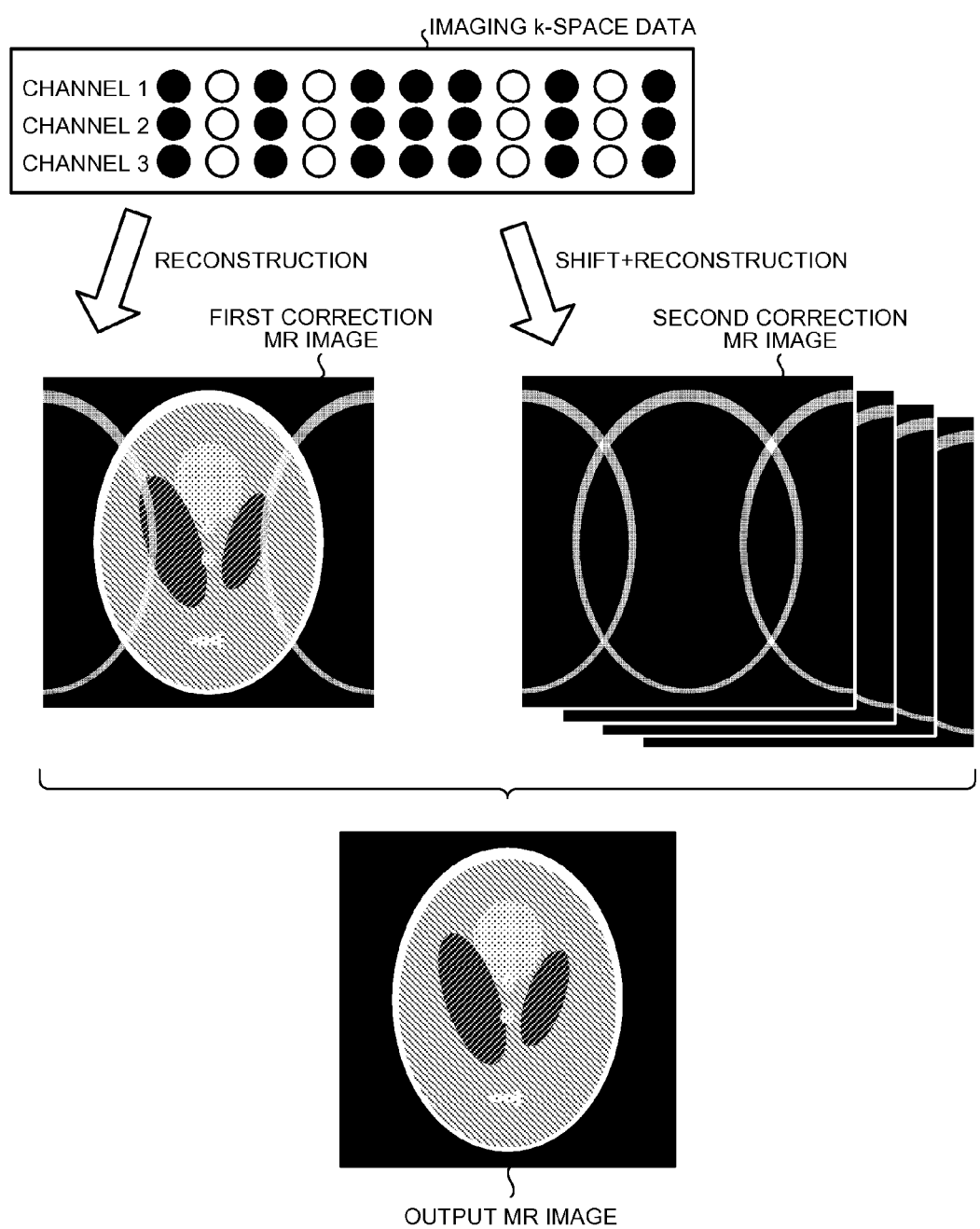
FIG. 5 is an explanatory diagram of processing to acquire an output MR image in the first embodiment.

Subsequently, an overview of a processing procedure in the first embodiment is explained. FIG. 4 is general flowchart of a processing procedure in the first embodiment. FIG. 5 is an explanatory diagram of processing to acquire an output MR image in the first embodiment. Suppose collection of k-space data has been performed by the k-space-data collecting unit 133a and k-space data of a processing object has been stored in the storage unit 132 before the processing procedure indicated in FIG. 4.

Terms used in the following are defined. First, an operation of sampling all grid points corresponding to output resolution is referred to as full sampling, and an operation of sampling some of grid points corresponding to output resolution is referred to as undersampling. Furthermore, each grid point is referred to as sampling position, and data at a sampling position at which sampling has been performed is referred to as known sample (black circles in FIG. 5), and data at a sampling position at which sampling is not performed by undersampling is referred to as unknown sample (white circles in FIG. 5). That is, the known sample has a sample value, and the unknown sample has no sample value.

Step S1: The correction-MR-image creating unit 133b reads k-space data of a processing object from the storage unit 132. In the first embodiment, this k-space data is obtained by performing sampling at same resolution as full sampling in a central region of a k-space, and by performing undersampling in a peripheral region of the k-space. The known samples maybe data obtained by sampling performed for each of channels.

Step S2: The correction-MR-image creating unit 133b creates a correction MR image using imaging k-space data read from the storage unit 132. For example, the correction-MR-image creating unit 133b creates k-space data having same resolution as full sampling by filing sample values at sampling positions at which known samples are not present in the imaging k-space data with zero. The correction-MR-image creating unit 133b then reconstructs the created k-space data, thereby creating a first correction MR image. This first correction MR image is an image that is created without processing a known sample of the imaging k-space data.

Moreover, the correction-MR-image creating unit 133b performs translation (shift) of the known sample according to rules prescribed separately, and creates new k-space data (hereinafter, shift k-space data as appropriate) having same resolution as full sampling. The correction-MR-image creating unit 133b then reconstructs the created shift k-space data, and thereby creates a second correction MR image. This second correction MR image is an image that is created by processing the known sample of the imaging k-space data. If the known sample is data corresponding to multiple channels, the correction-MR-image creating unit 133b creates the second correction MR image for all of the channels.

For example, the correction-MR-image creating unit 133b shifts the known sample on the k-space according to rules of translation prescribed separately. Subsequently, the correction-MR-image creating unit 133b regards a sample value at a sampling position that satisfies the condition that a sample value subjected to translation is present, and a known sample is not present as a sample value that is subjected to translation, and a sample value at a sampling position other than that as zero, to create shift k-space data having same resolution as full sampling. The correction-MR-image creating unit 133b then creates the second correction MR image in which the k-space data is reconstructed.

Step S3: The weighting-factor deriving unit 133c derives a weighting factor. For example, the weighting-factor deriving unit 133c estimates a weighting factor using a region in which full sampling is performed among imaging k-space data. For example, the weighting-factor deriving unit 133c estimates a weighting factor when a sample value at a sampling position is expressed by a weighted linear sum of sample values therearound using data constraint equivalent to Equation (4) in a region at which full sampling is performed, assuming that a sample value at a sampling position in k-space is expressed by a weighted linear sum of sample values therearound. In other words, the weighting-factor deriving unit 133c estimates a weighting factor, regarding a term that decreases the difference between a sample value at each sampling position in k-space data of interest and a weighted linear sum of sample values at sampling positions around the k-space data of all channels as data constraint. Because all values are known in a region in which full sampling is performed, a weighting factor can be estimated, for example, by using the method of least squares. When the method of least squares is expressed as a data term of a minimization problem, the weighting-factor deriving unit 133c can express as a total sum of values (errors) obtained by squaring differences between the left side and the right side of Equation (4) with respect to all of the sampling positions "k" in a region in which full sampling is performed. By solving the minimization problem to this total sum, a weighting factor $w(b, c, c_{out})$ can be estimated.

The weighting factor estimated here is to be a weighting factor that is used in a weighted linear sum of correction MR images at step S4. Because the Fourier transform is a linear transform, the weighting factor estimated using the data constraint equivalent to Equation (4) can be used as it is as a weighting factor of a weighted linear sum of correction MR images, maintaining the relation of Equation (4) also in an image space after the Fourier transform. Acquiring the weighting factor w for each combination of the shift amount b and the coil c in Equation (4) corresponds to acquiring a weighting factor that is used for a weighted linear sum of correction MR images for each combination of a rule of translation and a channel.

Step S4: The output-MR-image calculating unit 133d calculates an output MR image. Specifically, the output-MR-image calculating unit 133d performs weighted addition by multiplying each of the correction MR images created at step S2 by the weighting factor that is derived at step S3, to calculate an output MR image as shown in FIG. 5. When multiple channels are input, and an output MR image is calculated for each of the channels, the processing from step S2 to step S4 should be applied to all of the channels.

Figure 6:
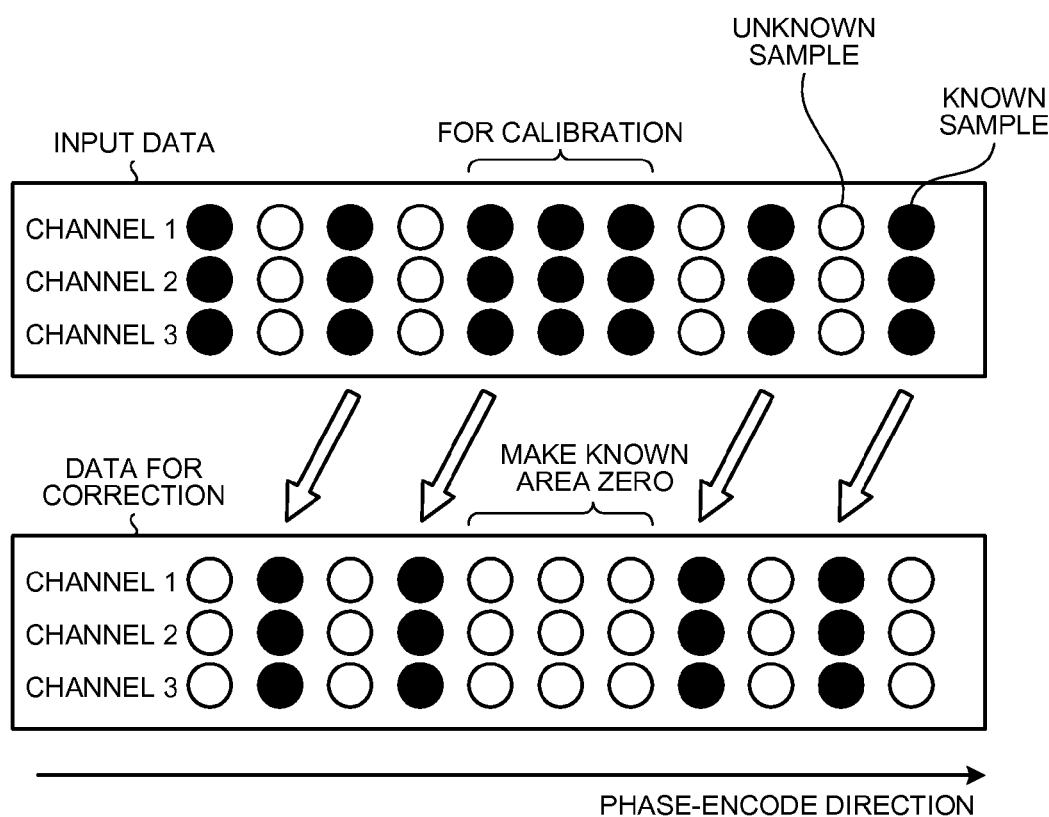
FIG. 6 is a diagram for explaining k-space data in the first embodiment.
Figure 7:
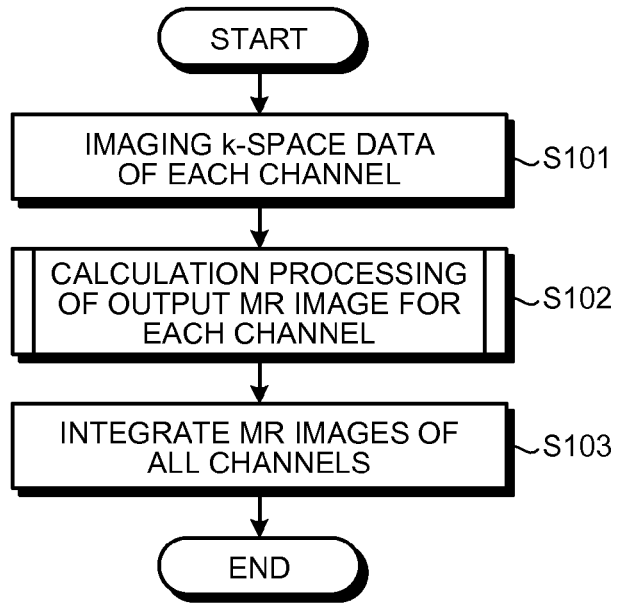
FIG. 7 is a flowchart of a processing procedure in the first embodiment.
Figure 8:
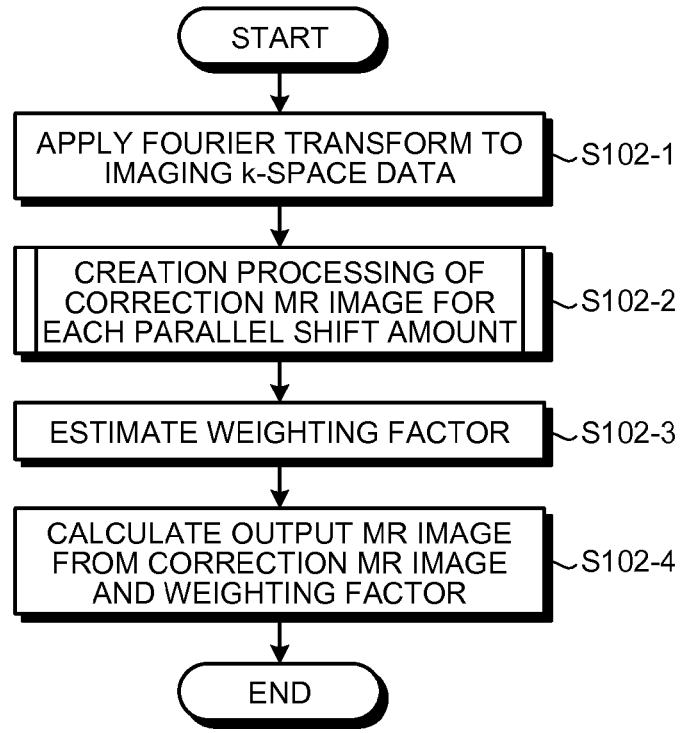
FIG. 8 is a flowchart of a processing procedure in the first embodiment.
Figure 9:
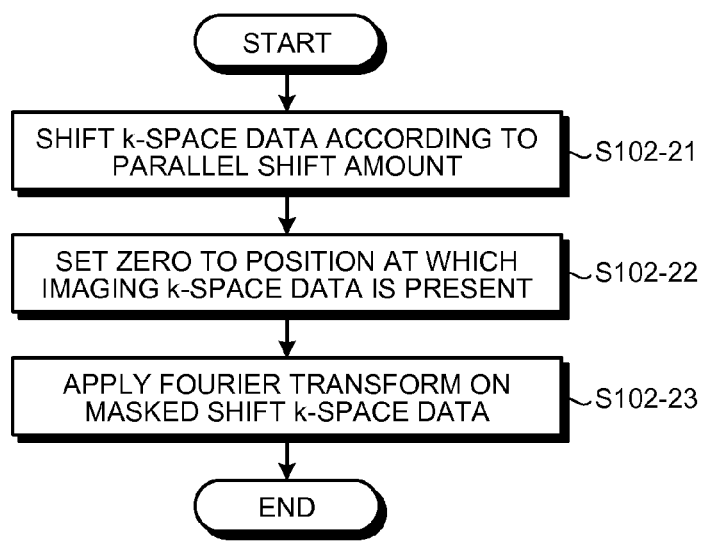
FIG. 9 is a flowchart of a processing procedure in the first embodiment.

Next, details of a processing procedure in the first embodiment are explained. FIG. 6 is a diagram for explaining k-space data in the first embodiment. FIGS. 7 to 9 are flowcharts of the processing procedure in the first embodiment. Although an example in which k-space data is of two dimensions is explained below, the embodiment is not limited thereto, and is similarly applicable to a case in which k-space data is of three dimension.

Step S101: The correction-MR-image creating unit 133b reads imaging k-space data of a processing object from the storage unit 132 for each channel (channel k=1, . . . , C). In the first embodiment, this imaging k-space data is obtained by performing sampling at same resolution as full sampling in a central region of a k-space, and by regularly performing undersampling in a peripheral region of the k-space by one line in a phase encode direction. Moreover, although illustration is omitted in FIG. 6, this imaging k-space data is obtained by performing sampling at same resolution as full sampling in a readout direction. The correction-MR-image creating unit 133b then creates k-space data having same resolution as full sampling by filling sample values at sampling positions at which a known sample is not present in the imaging k-space data with zero.

Step S102: For the imaging k-space data of each channel created at step S101, processing indicated at steps S102-1 to S102-4 is performed. The processing indicated at steps S102-1 to S102-4 is performed eight times if the number of channels is, for example.

Step S102-1: The correction-MR-image creating unit 133b creates a first correction MR image by applying the Fourier transform on imaging k-space data of a channel of interest.

Step S102-2: The correction-MR-image creating unit 133b performs translation according to rules prescribed separately, using the imaging k-space data of the channel of interest, and creates a second correction MR image by reconstructing shift k-space data after the translation. Moreover, the correction-MR-image creating unit 133b performs processing at steps S102-31 to S102-33 for each translation amount of each channel. For example, it is assumed that the rule of translation defines six kinds of translation amounts, (Readout, Phase Encode)=(0, 1), (0, −1), (1, 1), (1, −1), (−1, 1), (−1, −1). These are six kinds of translations by 2×3 with two kinds (phases +1 and −1) in the phase encode direction, and three kinds (phases +0, +1, and −1) in a readout direction.

In this case, the correction-MR-image creating unit 133b performs the processing at steps S102-31 to S102-33 for each of the six kinds of translation amounts for one channel. Moreover, if the number of channels is 8, the correction-MR-image creating unit 133b performs the processing at steps S102-21 to S102-23 48 times. Although in the first embodiment, an example in which six kinds of translations are performed has been explained, this is only one example, and for example, a single kind of translation may be performed.

Step S102-21: The correction-MR-image creating unit 133b shifts the imaging k-space data by a translation amount of interest. For example, the correction-MR-image creating unit 133b first translations the entire imaging k-space data by 1 in the phase encode direction as shown in FIG. 6, when the translation rule is (Readout, Phase Encode)=(0,1).

Step S102-22: Next, the correction-MR-image creating unit 133b sets zero in a sampling position of a known sample in the imaging k-space data among shift k-space data after the translation, to create a masked shift k-space data. This masked shift k-space data is k-space data in which a sample value is present only at a sampling position of an unknown sample in the imaging k-space data.

Step S102-23: The correction-MR-image creating unit 133b then applies the Fourier transform to the masked shift k-space data that is created at step S102-22, to create a second correction MR image.

Step S102-3: Thus, the correction-MR-image creating unit 133b creates respective second correction MR images according to the six kinds of translation amounts for all of the channels. For example, if the number of channels is 8, the correction-MR-image creating unit 133b creates 48 pieces of the second correction MR images. When the first correction MR image created from the imaging k-space data is X0, the second correction MR image created from masked shift k-space data of each channel c=1, . . . , C is Xi (i=1, . . . , C), the output MR image X can be expressed by Equation (7) that is Equation (6) where the weighting factor w0=1.

$$X = X_0 + \sum_{i=1}^{C} w_i X_i \quad (7)$$

In this example, the correction MR images are the first correction MR image X0 and the second correction MR image Xi (i=1, . . . , C). Because the Fourier transform is a linear transform, calculating the output MR image as a weighted addition of the first correction MR image X0 and the second correction MR image Xi is equivalent to calculating a weighted addition of the weighting factor wi for the imaging k-space data and the masked shift k-space data and then reconstructing by the Fourier transform. Moreover, the masked shift k-space data has a value not "zero" only at a sampling position of an unknown sample in the imaging k-space data, and is created by operation of translating the entire imaging k-space data in the phase encode direction. This operation is mathematically equivalent operation to the linear interpolation of a k-space. Therefore, in this case, the weighting factor can be estimated by solving the minimization problem using the data constraint equivalent to Equation (4). In addition, as described later, by combining with a constraint equation other than the data constraint of Equation (4), performance of the PI can be improved.

Thus, the weighting-factor deriving unit 133c estimates a weighting factor using the data constraint equivalent to Equation (4). For example, the weighting-factor deriving unit 133c estimates a weighting factor for each of the second correction MR images so that an error in data constraint becomes small. Furthermore, in the first embodiment, the weighting factor of the first correction MR image is "1".

Step S102-4: The output-MR-image calculating unit 133d multiplies each correction MR image by a corresponding weighting factor, and obtains the total sum thereof as an output MR image of the channel of interest.

Step S103: Moreover, the output-MR-image calculating unit 133d integrates output MR images of all channels to acquire a final output MR image. For example, the output-MR-image calculating unit 133d calculates a mean value of square sum of the output MR images of all channels, to acquire the final output MR image. The final output MR image here is only expression to distinguish from the output MR image for convenience sake of explanation. For example, the MR image that is obtained by performing post processing on the final output MR image can be output finally to the display unit 135, and the like.

Modification of First Embodiment

Although a technique of applying the same rule of translation to the entire k-space data has been explained in the first embodiment described above, the embodiment is not limited thereto. A technique in which a rule of translation is prescribed for each sampling position, and sampling positions to which the same rule of translation is applied are grouped, and the second correction image Xi thus is generated may be applied. For example, it may be implemented by replacing a part of the processing procedure explained so far may with a processing procedure described below. A technique explained below is a technique of prescribing a rule of translation for each sampling position, and therefore, variable sampling densities are supported.

Step S201: The correction-MR-image creating unit 133b prescribes a rule of translation for each of sampling positions of unknown samples in imaging k-space data. The rule of translation may be prescribed in advance.

Figure 10:
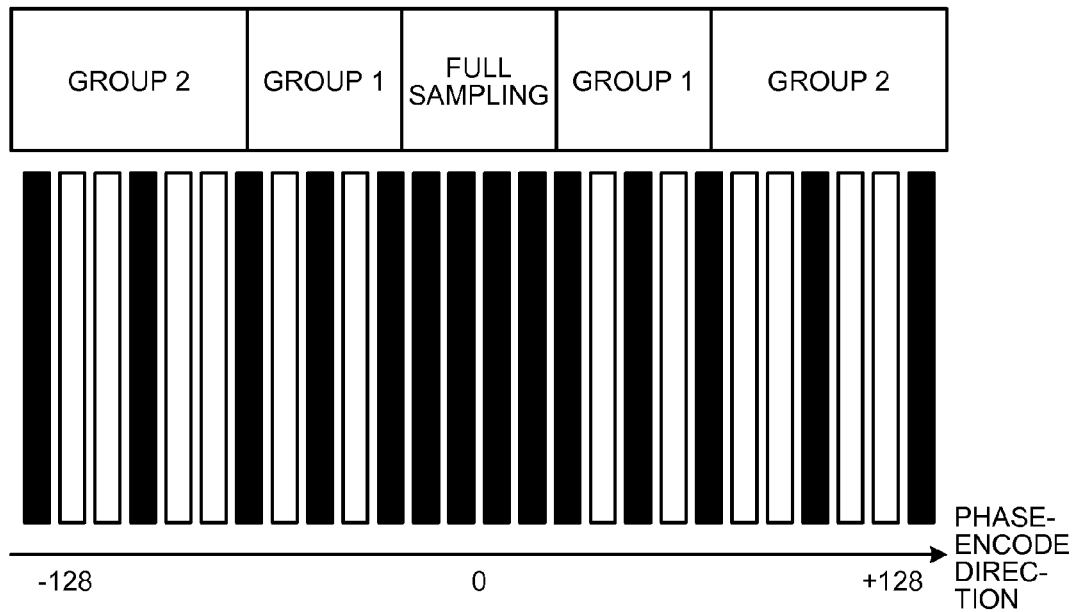
FIG. 10 is a diagram for explaining a modification of the first embodiment.

Step S202: The correction-MR-image creating unit 133b groups sampling positions to which the same rule of translation is applied in shift k-space data as a set of sampling positions that have the same weighting factor wi. FIG. 10 is a diagram for explaining a modification of the first embodiment. For example, as shown in FIG. 10, when k-space data is collected by two-dimensional Cartesian sampling, an example in which full sampling is performed in a central part, sampling on every ½ line is performed in a apart close to the central part out of a peripheral part, and sampling on every ⅓ is performed in a part other than those to collect data is considered. At this time, making two groups, a first group (Group 1) of regions in which sampling of every ½ line is performed and a second group (Group 2) of regions in which sampling of every ⅓ is, a rule of translation, (Readout, Phase Encode)=(0, 1), (0, −1), (1, 1), (1, −1), (−1, 1), (−1, −1) is used for Group 1, and a rule of translation, (Readout, Phase Encode)=(0, 1), (0, −1), (1, 1), (1, −1), (−1, 1), (−1, −1), (0, 2), (0, −2), (1, 2), (1, −2), (−1, 2) (−1, −2) is used for Group 2. At this time, a sample that is translated out to a group is a masking subject (that is, the sample value is set to zero). Furthermore, even if the translation amount is same, when belonging to a different group, it is handled as separate translations. The correction-MR-image creating unit 133b is not necessarily required to put all sampling positions to which the same rule of translation is applied in a single group.

Step S203: The correction-MR-image creating unit 133b creates the second correction MR image Xi for each group, each rule of translation, and each channel. As described above, when different rules of translation are applied to respective groups, the second correction image Xi is created in number corresponding to the product of the total sum of all groups corresponding to the number of rules of translation and the number of channels.

Step S204: The weighting-factor deriving unit 133c creates data constraint equation equivalent to Equation (4) corresponding to each rule of translation (as described above, even if the translation amount is same, if belonging to different groups, translations are handled as different translations), and estimates the weighting factor wi using the created data constraint equation. Specifically, the weighting-factor deriving unit 133c creates a constraint equation of Equation (4) using full sampling regions for respective rules of translation of respective groups, and such a weighting factor that minimizes the data constraint based on Equation (4) that is the total sum of errors. For example, the weighting-factor deriving unit 133c creates a constraint equation of Equation (4) using a full sampling region for each of the rule of translation applied to the region of Group 1 and the rule of translation applied to the region of Group 2 in each channel, and estimates such a weighting factor that minimizes the data constraint based on Equation (4) that is the total sum of errors.

Step S205: The output-MR-image calculating unit 133d multiplies each correction MR image by a corresponding weighting factor, and obtains the total sum thereof as an output MR image of a channel of interest.

Effect of First Embodiment

As described above, according to the first embodiment, a high quality output MR image can be acquired from k-space data that is collected with less samples than full sampling.

Second Embodiment

Although a technique of deriving a weighting factor using a constraint equation (data constraint) that is acquired from sampled data in the first embodiment, the embodiment is not limited thereto. A technique of data constraint is not limited to the technique explained in the first embodiment. For example, a weighting factor may be derived by combination of data constraint and prior constraint (by prior knowledge). Moreover, a weighting factor may be derived only by prior constraint, for example.

The data constraint is explained again. When k-space data that corresponds to an output MR image is expressed as Y, k-space data that corresponds to each of the second correction MR images Xi is expressed as Yi, a matrix to extract a region used for full sampling from the entire k-space data is expressed as M, and a vector in which weighting factors are aligned is expressed as w, the data constraint corresponds to solving a optimization problem expressed by Equation (8). Although weights are equal in each member of the data constraint in this Equation (8), weights may be taken into consideration.

$$w = \operatorname*{argmin}_{w} E_{data}(w) = \operatorname{argmin} \left\| M\left(\sum_i w_i Y_i - Y\right) \right\|_2^2 \quad (8)$$

Furthermore, the weighting-factor deriving unit 133c can add prior constraint (by prior knowledge) at deriving a weighting factor. As described above, the weighting factor w is a factor of the second correction MR image Xi, and from Equation (5), the output MR image X is a function of the weighting factor w. Therefore, when the output MR image is expressed as X(w), and a function to evaluate error from the data constraint is expressed as $E_{data}$(w), and a function to evaluate error from the prior constraint is expressed as $E_{prior}$(w) and a parameter to adjust the balance between the data constraint and the prior constraint is expressed as λ, the weighting factor is derived by Equation (9).

$$w = \operatorname*{argmin}_{w}\{E_{data}(w) + \lambda E_{prior}(w)\} \quad (9)$$

The weighting-factor deriving unit 133c may solve the minimization problem of this Equation (9) to estimate the weighting factor w. The output-MR-image calculating unit 133d calculates and outputs the output MR image (w). Because an estimation problem of a weight w is a minimization problem of an energy function of Equation (10), a framework of existing energy minimization can be used as it is.

$$E(w) = E_{data}(w) + \lambda E_{prior}(w) \quad (10)$$

The weighting-factor deriving unit 133c can acquire a least square when $E_{prior}$(w)=0 and $E_{data}$(w) is a quadratic constraint equation. As for an energy function other than that, although it is dependent on a form of energy function, either the gradient descent method, the conjugate gradient method, or the nonlinear conjugate gradient method is often applicable. An energy minimization method other than the methods exemplified here can also be applied.

Subsequently, the prior constraint is explained. Giving the function $E_{prior}$(w) to evaluate error from the prior constraint as a function of the output MR image X(w) is considered. Expressing it as $E_{prior}$(w)=f(X(w)) where f is a function of an MR image, when expressed in a formula, is considered. At this time, because the function f is a function for an image, the same prior as the prior constraint used in image reconstruction or noise removal can be used. For example, the following prior constraint can be applied. Note that respective techniques explained below can be combined as appropriate.

(Technique 1) The weighting-factor deriving unit 133c can apply a prior constraint of regularization by a template image (reference image). For example, the weighting-factor deriving unit 133c applies a prior in which the function f is defined as Equation (11). Although L2 norm is used in Equation (11), another norm (for example, L1 norm in Equation (12)) can be used as compressed sensing.

$$f(X) = \|X - X_0\|_2^2 \quad (11)$$

$$f(X) = \|X - X_0\|_1 \quad (12)$$

As a template image X0, following can be used. For example, when data collected successively in time series is present in the MRI apparatus 100, the weighting-factor deriving unit 133c can use an image of a previous frame in chronological order as the template image X0. Note that an image of a previous frame is only one example. As long as it is an image of a frame for which a certain degree of correlation is recognized in chronological order, not only of a previous frame, but also an image of a following frame, of some frames before, and of some frames later can be used as the template image X0.

Furthermore, for example, when slab imaging in which a region including multiple slices is the imaging region is performed in the MRI apparatus 100, the weighting-factor deriving unit 133c can use another slice in the same slab as the template image X0.

Moreover, when multiple protocols are successively executed in the MRI apparatus 100, the weighting-factor deriving unit 133c can use an image collected by another protocol to be created as the template image X0. For example, in the MRI apparatus 100, there is a case in which multiple protocols such as preparation scanning including a protocol to collect positioning images, and a protocol to collect sensitivity maps, and imaging scanning including a protocol to collect T1 emphasizing image, and a protocol to collect T2 emphasizing image are successively executed. In such a case the weighting-factor deriving unit 133c can use, for example, a positioning image that is collected by the protocol to collect positioning images as the template image X0. Furthermore, for example, the weighting-factor deriving unit 133c can use an image acquired among protocols in imaging scanning as the template image X0.

In addition, the template image X0 is not necessarily required to be an image of the subject himself/herself, and may be an image acquired by some kind of study.

(Technique 2) The weighting-factor deriving unit 133c can apply prior constraint in which a signal value of a specific region is assumed to be zero. For example, when a matrix to extract a region in which a signal value is zero for the MR image X is expressed as $M_{zero}$, the weighting-factor deriving unit 133c applies the prior in which the function f is defined as Equation (13).

$$f(X) = \|M_{zero} X\|_2^2 \quad (13)$$

The specific region here is, for example, a region for which it is obvious that a signal value is zero such as regions at four corners when an image of an external of a subject or brains is imaged.

(Technique 3) The weighting-factor deriving unit 133c can apply prior constraint that uses the sparse transform (for example, the wavelet transform and the total variation). This prior constraint is known as the name of the compressive sensing technique. For example, when the sparse transform is ψ, the weighting-factor deriving unit 133c applies prior in which the function f is defined as Equation (14).

$$f(X) = \|\Psi X\|_1 \quad (14)$$

Moreover, the weighting-factor deriving unit 133c may use two or more kinds of sparse transforms. When ψ1, ψ2 are sparse transforms, and λ1, λ2 are parameters, the weighting-factor deriving unit 133*c* applies prior in which the function f is defined as Equation (15).

$$f(X)=\lambda_1\|\Psi_1 X\|_1+\lambda_2\|\Psi_2 X\|_1 \qquad (15)$$

(Technique 4) The weighting-factor deriving unit 133*c* can apply prior constraint in which two or more of the prior constraints from Technique 1 to Technique 3 described above are combined. In this case, the weighting-factor deriving unit 133*c* defines the function f by weighted addition of the functions f acquired from the above respective equations.

As indicated by these examples, as a result of combining knowledge specific to an image space as a prior constraint with data constraint, further precise image reconstruction can be achieved. This processing can be explained that an output MR image is expressed in a partial space based on multiple pieces of channel data and then estimated by using data constraint and prior constraint in the partial space.

Another Embodiment

Embodiments are not limited to the first and the second embodiments describe above.

Formulation: Translation Pattern for Time-Series Imaging

Figure 11:
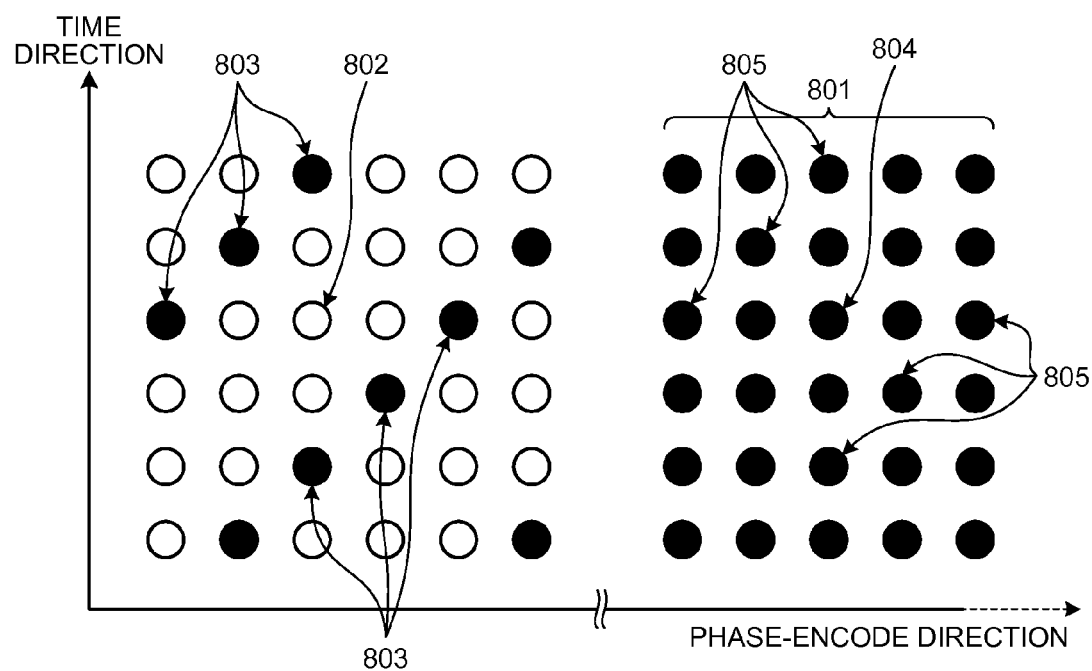
FIG. 11 is a diagram for explaining k-space data in another embodiment.

The embodiments described above can be applied similarly to reconstruction of time-series k-space data. When time-series k-space data is reconstructed, a technique called "k-t GRAPPA" is used in some cases. FIG. 11 is a diagram for explaining k-space data in another embodiment.

As shown in FIG. 11, the k-space-data collecting unit 133*a* performs sampling while thinning out at ¼ at each time, and the sampling is performed while shifting a sampling position every one unit time. In FIG. 11, a sampling position 802 indicates a sampling position having no sample value, a sampling position 803 indicates a sampling position having a sample value that is used for estimation of the sampling position 802. Moreover, a region 801 is assumed to be subjected to full sampling as data for calibration.

For example, the sampling position 802 is considered to be created by translating each point at the sampling positions 803 in the phase encode direction and a time direction. The correction-MR-image creating unit 133*b* applies the Fourier transform to each translation pattern, to create the second correction MR image Xi. At estimation of the weight wi, the weighting-factor deriving unit 133*c* can use, as data constraints, a sampling position 804 and a sampling position 805 at same relative position in a time space in the region 801 in which full sampling has been performed.

Data Constraint Using Divided Region

The embodiments describe above are applicable even when a region of k-space is divided. The radial GRAPPA is one implementation of GRAPPA to k-space data that is acquired by radial scanning in which k-space data is acquired by scanning a line segment that passes through the center of a k-space while changing the angle thereof (by non-Cartesian). In this technique, scanning is divided into groups (segments) based on a criterion separately prescribed, and data in each segment is regarded as one acquired approximately by Cartesian, and GRAPPA is applied to individual segment.

When a region is divided as in the radial GRAPPA, for example the correction-MR-image creating unit 133*b* applies reconstruction by the non-uniform Fourier transform (NuDFT) to imaging k-space data that is given as input, and an MR image thus acquired is to be the first correction MR image X0. Furthermore, the correction-MR-image creating unit 133*b* reconstructs k-space data for correction that is created in individual divided region, and an MR image thus acquired is to be the second MR image Xi. Furthermore, the weighting-factor deriving unit 133*c* gives a data constraint to individual divided region similarly to the embodiment described above.

Technique of Creating Correction MR Image for Arbitrary Trajectory

Figure 12:
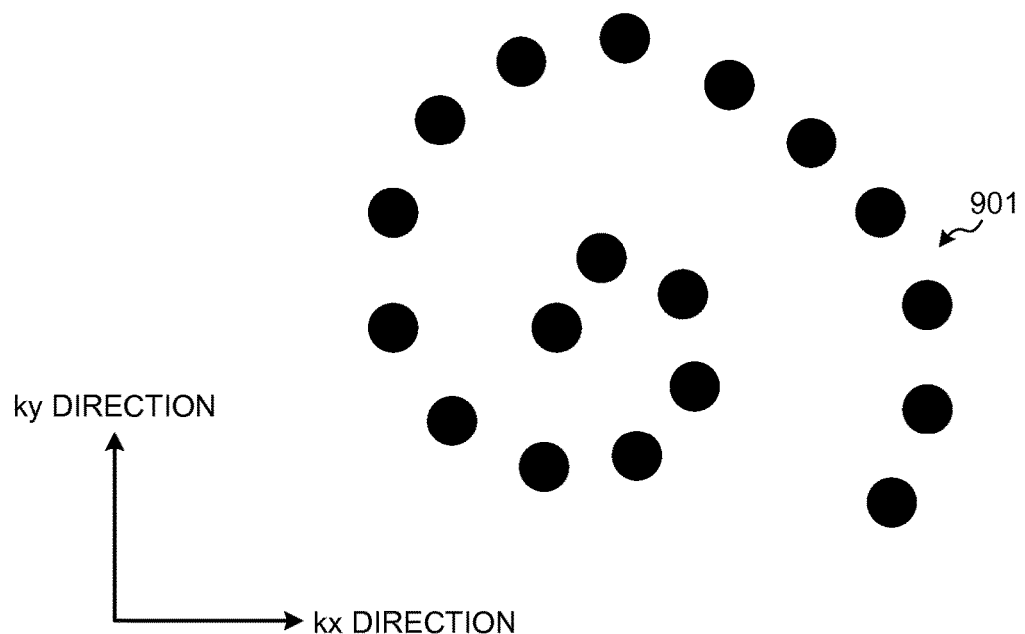
FIG. 12 is a diagram for explaining k-space data in another embodiment.
Figure 13:
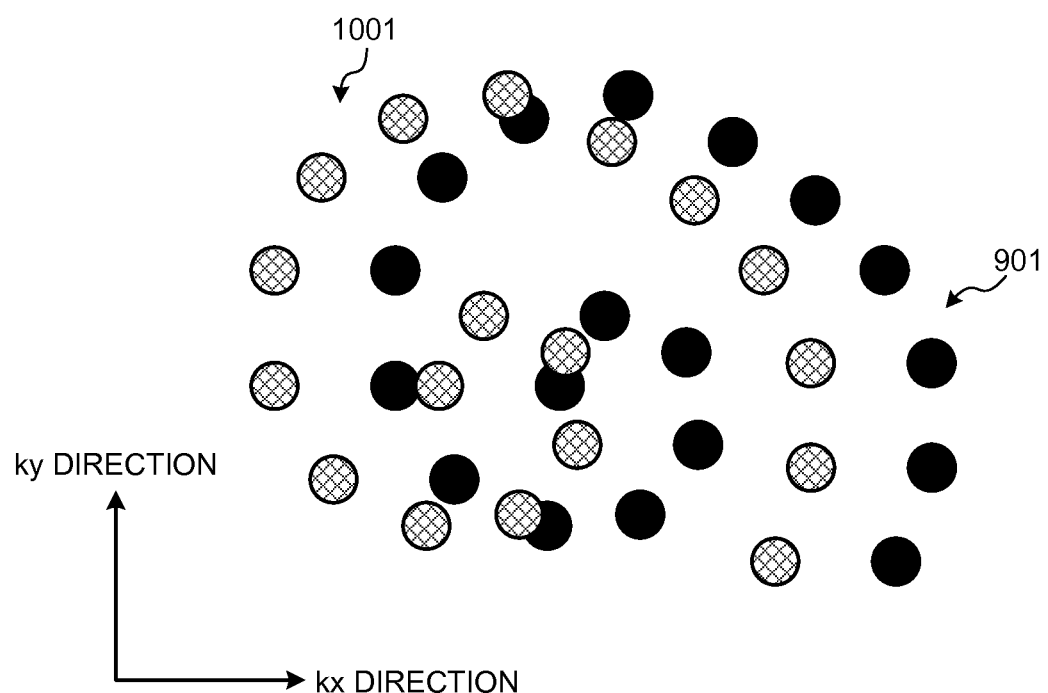
FIG. 13 is a diagram for explaining k-space data in another embodiment.
Figure 14:
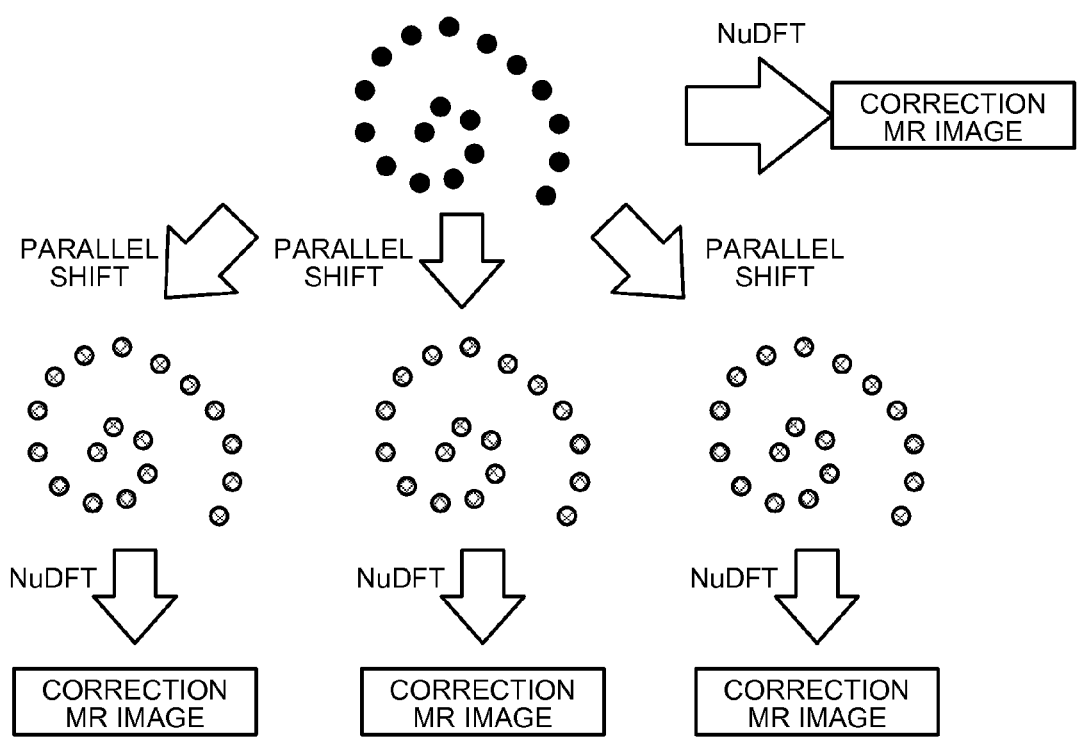
FIG. 14 is a diagram for explaining k-space data in another embodiment.

Depending on a type of non-Cartesian sampling, there is a case in which GRAPPA designed for the above Cartesian or radial is not applicable. FIGS. 12 to 14 are diagrams for explaining k-space data in another embodiment.

For example, to spiral scanning shown in FIG. 12, the Technique for the Cartesian or radial scanning describe previously is not applicable. In such a case, more than one group of translation pattern on a k-space is determined in advance. The correction-MR-image creating unit 133*b* applies the translation pattern to a set of points having sample values for each group, and creates a set of points on the k-space. The correction-MR-image creating unit 133*b* then applies reconstruction by the non-uniform Fourier transform (NuDFT) to the created set of points, to acquire the second correction image Xi (for example, refer to FIG. 14).

An example in which a set of points 901 (a set of dots of black circle in spiral in FIG. 13) having sample values in FIG. 12 is translated by a unit amount in a kx direction is shown in FIG. 13. In FIG. 13, a set of points 1001 having a pattern with circles in spiral are points created by translating the set of points 901, and for these points, weighting factors of respective channels are considered to be totaled. Note that the set of points 1001 is not required to include all points in the set of points 901, and some points may be excluded.

The NuDFT includes operation to correct non-uniformity in the sampling density in some form (for example, if a technique in which it is returned back to Cartesian FFT through the technique called gridding is used, operation of correcting non-uniformity in the density by division of a weight value that is dependent on a position is performed). For that part, the entire k-space including the translated k-space data that is used to create all of the second correction MR images Xi is used as sampling data, to calculate the sampling density thereof, thereby correcting the non-uniformity based thereon.

Creation of k-Space Data

Although an example in which processing of translation is performed at the time of creating, from imaging k-space data, another k-space data has been explained in the above embodiment, the embodiment is not limited thereto. For example, when data collected successively in time series is present in the MRI apparatus 100, the correction-MR-image creating unit 133*b* may use k-space data at other point of time, as k-space data different from the imaging k-space data. For example, the correction-MR-image creating unit 133*b* can give a sample value to an unknown sample in the imaging k-space data by using k-space data at an adjacent time point in chronological order, to create another k-space data.

Alternatively, for example, the correction-MR-image creating unit 133*b* can give a sample value to an unknown sample in the imaging k-space data by performing GRAPPA on the imaging k-space data, to create another k-space data.

Furthermore, although a technique in which processing of translation is performed on imaging k-space data has been explained in the above embodiment, a concept of principal component analysis (PCA) may be further introduced thereto. For example, in the embodiment described above, processing of translation is performed on the respective imaging k-space data acquired at all channels, and all of these are to be objects of weighted addition. However, the embodiment is not limited thereto, and a channel to be an object of the weighted addition may be reduced based on the concept of principal component analysis. As a result, the amount of calculation can be reduced, and an effect of reducing influence of noise can also be expected.

Moreover, although a technique in which processing of translation is performed on imaging k-space data in a k-space has been explained in the above embodiment, the processing of translation can be performed not in a k-space but in an image space after the Fourier transform. For example, a case in which an image space is of one-dimensional is explained as an example. In this case, when original data in the k-space is expressed as k(x), data translated by a in the k-space is expressed as k(x−a). When the inverse discrete Fourier transform of the original data k(x) is expressed as T(k(x)), translated data T(k(x−a)) is expressed by Equation (16). exp(2πiax/N) in Equation (16) indicates the (2πiax/N)-th power of the base of natural logarithm (Napier's constant) e.

$$T(k(x-a)) = T(k(x)) \cdot \exp(2\pi i a x/N) \qquad (16)$$

Therefore, by multiplying each position x by exp(2πiax/N), translation can be performed in an image space. By performing the technique of translation as described above on each of two or more coordinate axes in an image space, translation can be achieved on an image space even when the image space is of two-dimensional or more.

Imaging k-Space Data

Although, the above embodiment assumes k-space data in which sampling at same resolution as full sampling is performed in a central region of a k-space and undersampling is performed in a peripheral region of the k-space as imaging k-space data, the embodiment is not limited thereto. Imaging k-space data is only required to be k-space data that has sample values at some of sampling positions of the k-space corresponding to full sampling. Moreover, sampling intervals when undersampling is performed may be variable (sampling intervals varying according to sampling positions).

Image Processing Apparatus

Furthermore, although an example in which the k-space-data collecting unit 133a of the MRI apparatus 100 collects k-space data, and processing by the correction-MR-image creating unit 133b, the weighting-factor deriving unit 133c, and the output-MR-image calculating unit 133d is performed on the collected k-space data has been explained, the embodiment is not limited thereto. For example, an image processing apparatus that is different from the MRI apparatus 100 may perform processing equivalent to the processing by the correction-MR-image creating unit 133b, the weighting-factor deriving unit 133c, and the output-MR-image calculating unit 133d on k-space data having less samples than those in full sampling. In this case, the image processing apparatus receives k-space data from the MRI apparatus or other external devices through a network, or receives k-space data through a recording medium, or the like. Moreover, how k-space data having less samples than those in full sampling is collected in the MRI apparatus 100 is not directly related to processing in the image processing apparatus. That is, k-space data having less samples than those in full sampling is not necessarily collected by undersampling, but may be one obtained by thinning out after k-space data is collected by full sampling. That is, it is only necessary to have k-space data with less samples than those in full sampling, as an object of processing.

Program

Instructions given in the processing procedure presented in the embodiment described above can be executed based on a software program. By recording this program by a general-purpose computer system in advance, and by reading this program, similar effects as the effects obtained by the MRI apparatus or the image processing apparatus of the embodiment described above can be achieved. The instructions described in the above embodiments are recorded as a program that can be executed by a computer, in a magnetic disk (a flexible disk, a hard disk, or the like), an optical disc (a compact-disc read-only memory (CD-ROM), a compact disc recordable (CD-R), a compact disc rewritable (CD-RW), a digital versatile disk (DVD)-ROM, a DVD±R, a DVD±RW, or the like), a semiconductor memory, or a recoding medium of a similar kind. As long as the recording medium can be read by a computer or an integrated system, the recording form can take any form. If a computer reads the program from this recording medium and executes the instruction described in the program based on this program by the CPU, a similar operation as that of the MRI apparatus and the image processing apparatus of the embodiment described above can be achieved. Of course, when the computer acquires or reads the program, the computer can acquire or read through a network.

Moreover, an OS (operating system) that operates on the computer, database management software, middleware (MW) of a network, etc. or the like can perform a part of each processing to achieve the embodiments described above based on instructions of the program that is installed in the computer or the integrated system from the recording medium. Further, the recording medium is not limited to a medium independent of the computer or the integrated system, and includes a recording medium that stores or temporarily stores the program by downloading the program that is transmitted through a local area network (LAN), the Internet, and the like. Moreover, the number of the recording medium is not limited to one, and a case where the processing in the embodiment described above is performed from more than one medium is also included in the recording medium in the embodiment, and the configuration of the medium can take any configuration.

The computer or the integrated system according to the embodiment is to perform each processing in the embodiment described above based on the program recorded in the recording medium, and can take any of configurations of a single-unit apparatus such as a personal computer and a microcomputer, a system in which multiple devices are connected through a network, and the like. Moreover, the computer in the embodiment is not limited to a personal computer, and includes an arithmetic processing unit included in an information processing device, a microcomputer, and the like, and is a generic term of a device and apparatus that can implement the functions in the embodiments by the program.

According to the magnetic resonance imaging apparatus and the image processing apparatus of at least one of the embodiments described above, image quality can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
   MRI system components including static and gradient magnetic field generators, radio frequency (RF) coils, RF transmitter and receiver circuits, at least one processor and a memory that stores processor-executable instructions that, when executed by the processor, cause the MRI apparatus to:
   acquire MR data providing partially sampled first k-space data;
   generate second k-space data by calculating and assigning a sample values to at least a part of sampling positions having no sample value in the first k-space data;
   reconstruct in the spatial domain a first image having pixel data values from the first k-space data;
   reconstruct in the spatial domain a second image having pixel data values from the second k-space data;
   generate pixel weighting factors for pixel data values in the first and second images; and
   generate a further magnetic resonance spatial domain image by performing weighted pixel data value additions of the reconstructed first and second images using the generated weighting factors.

2. The magnetic resonance imaging apparatus according to claim 1, wherein, an assigned sample value in the second k-space data is determined based on a sample value that has been acquired for sampling positions in the first k-space data.

3. The magnetic resonance imaging apparatus according to claim 1, wherein, an assigned sample value in the second k-space data comprises a sample value of the first k-space data at a sampling position having specific positional relation to the sampling positions having no sample value in the first k-space data.

4. The magnetic resonance imaging apparatus according to claim 1, wherein, assigned sample values in the second k-space data compris specific values of the first k-space data at respectively corresponding sampling positions having a sample value.

5. The magnetic resonance imaging apparatus according to claim 1, wherein, assigned sample values in the second k-space data comprise sample values of respectively corresponding non-sampled positions in the first k-space data by assigning a translated there-into first k-space sampled position data value so as to create the second k-space data from the first k-space data.

6. The magnetic resonance imaging apparatus according to claim 1, wherein, the weighting factors are derived using a constraint equation in which a sample value of each sampling position in k-space data of a channel of interest is equal to a weighted linear sum of sample values at sampling positions located there-around in k-space data of all channels including channels other than the channel of interest.

7. The magnetic resonance imaging apparatus according to claim 1, wherein, the weighting factors are determined so as to decrease a difference between a pixel value at a reference image having identical resolution with the magnetic resonance image and a pixel value of the further magnetic resonance image.

8. The magnetic resonance imaging apparatus according to claim 1, wherein, the weighting factors are determined assuming that a MR signal value of a specific region in the magnetic resonance image is zero.

9. A diagnostic medical magnetic resonance (MR) image processing apparatus comprising:
   a source of partially sampled MR first k-space data;
   a processor coupled to receive said first k-space data from said source and a memory that stores processor-executable instructions that, when executed by the processor, cause the processor to:
   generate second k-space data by calculating and assigning sample values to at least a part of sampling positions having no sample value in the first k-space;
   reconstruct in the spatial domain a first image having pixel data values from the first k-space data;
   reconstruct in the spatial domain a second image having pixel data values from the second k-space data;
   generate pixel weighting factors for pixel data values in the first and second images; and
   generate a further magnetic resonance spatial domain image by performing weighted pixel data value additions of the reconstructed first and second images using the generated weighting factors.

10. A magnetic resonance imaging (MRI) apparatus comprising:
    MRI system components including static and gradient magnetic field generators, radio frequency (RF) coils, RF transmitter and receiver circuits, at least one processor and a memory that stores processor-executable instructions that, when executed by the processor, cause the MRI apparatus to:
    acquire MR data providing partially sampled first k-space data;
    generate second k-space data from the first k-space data having a sample value at a part of sampling positions on a k-space corresponding to full sampling;
    reconstruct in the spatial domain a first image having a fold-over from the first k-space data;
    reconstruct in the spatial domain a second image from the second k-space data; and
    generate a further magnetic resonance image without a fold-over by performing weighted addition of first and second images.

* * * * *